United States Patent
Akimoto et al.

[11] Patent Number: 5,270,335
[45] Date of Patent: Dec. 14, 1993

[54] METHOD OF INHIBITING METABOLISM OF CHOLESTEROL

[75] Inventors: Kengo Akimoto, Osaka; Sumio Asami, Ibaraki; Michihiro Sugano, Fukuoka; Nobuaki Hirose, Fukuoka, all of Japan

[73] Assignee: Suntory Limited, Osaka, Japan

[21] Appl. No.: 779,998

[22] Filed: Oct. 21, 1991

[30] Foreign Application Priority Data

Oct. 22, 1990 [JP] Japan .................... 2-281839

[51] Int. Cl.$^5$ ............................ A61K 31/34
[52] U.S. Cl. ........................ 514/470; 514/469
[58] Field of Search ................ 514/469, 470

[56] References Cited

FOREIGN PATENT DOCUMENTS 0409654 7/1990 European Pat. Off. ........ 31/34

OTHER PUBLICATIONS

Nobuaki Hirose et al., "Inhibition of cholesterol absorption and synthesis in rats by sesamin," Journal of Lipid Research, vol. 32, 1991, pp. 629-638.
Michihiro Sugano et al., "Influence of Sesame Lignans on Various Lipid Parameters in Rats," Agric. Biol. Chem., 54(10), 1990, 2669-2673.
Patent Abstracts of Japan, vol. 13, No. 326 (C-620) [3674], Jul. 24, 1989.
The Merck Index, #8418, 11th Ed., 1989.
CA 114(1):5257w, Sugano et al., 1990.

Primary Examiner—Frederick E. Waddell
Assistant Examiner—Kimberly R. Jordan
Attorney, Agent, or Firm—Burns, Doane, Swecker & Mathis

[57] ABSTRACT

A method of inhibiting the metabolism of cholesterol, comprising administering to a subject a pharmaceutical composition comprising a dioxabicyclo[3.3.0]octane derivative represented by the following general formula (I):

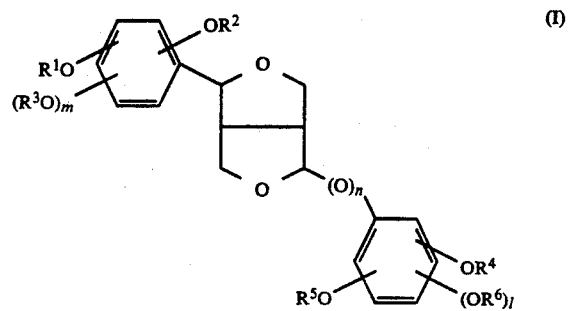

wherein $R^1$, $R^2$, $R^3$, $R^4$, $R^5$ and $R^6$ independently represent a hydrogen atom or an alkyl group having 1 to 3 carbon atoms, or $R^1$ and $R^2$ and/or $R^4$ and $R^5$ together form a methylene group or an ethylene group, and n, m and l are 0 or 1.

4 Claims, No Drawings

METHOD OF INHIBITING METABOLISM OF CHOLESTEROL

BACKGROUND OF THE INVENTION

1. Field of the Invention

The present invention relates to a method of inhibiting the metabolism of cholesterol, and the use of dioxabicyclo [33.0] octane derivative for producing a pharmaceutical preparation to be used for inhibiting the metabolism of cholesterol.

2. Description of the Related Art

Cholesterol is the main sterol of higher animals, present in all the tissues, an important component of the cell wall, and is used in vivo in a large amount as a starting material of the bile acids. Cholesterol is synthesized in the liver and other organs, and further intaken from the food. However, it is epidemiologically believed that a large amount of intake of saturated fatty acids or cholesterol provides a relatively high concentration of serum cholesterol and a high mortality due to coronary heart diseases. Therefore, to treat diseases caused by hypercholesteremia, cholesterol intake inhibitors, accelerators of disassimilatory excretion of cholesterol to the bile acids, or cholesterol biosynthesis inhibitors are used. On the other hand, it is epidemiologically recognized that there is a positive correlations between the amount of fat intake and a mortality from colon cancer. Namely, according to epidemiological research, the morbidity rate of colon cancers is found to positively correlate with an amount of intake of fat and protein (Wynder Cancer Res., 35,33 88, 1975). An increase of the intake of animal fat is related to an increase of cholesterol, and a role of metabolites thereof by enteric bacteria in the oncogenesis is noted. It is known that cholesterol is metabolized to neutral steroids such as coprostanol, coprostanone, cholestanol and the like, and in the area having a high risk of colonic cancers, a concentration of neutral steroids in the feces is high. Moreover, it is reported that cholesterol dehydrogenase, which is known as an enzyme converting cholesterol to coprostanol, is present at a high level in patients suffering from colon cancer.

Moreover, an amount of animal fat highly correlates with mortality due to breast cancer, and this phenomenon is explained in that a high animal fat food increases the amount of excretion of the bile acids and cholesterol into the bile, and they are metabolized by enteric bacteria to estrogen, which then promotes oncogenesis of breast cancer.

Nevertheless, currently, there are no known substances which inhibit the metabolism of primary bile acids and cholesterol.

Accordingly, a new method of inhibiting the metabolism of cholesterol is urgently sought.

SUMMARY OF THE INVENTION

Accordingly, the present invention provides a new method of inhibiting the metabolism of cholesterol by enteric microbial flora, and the use of dioxabicyclo[3.3.0]octane for producing pharmaceuticals used to inhibit the metabolism of cholesterol.

More specifically, the present invention provides a method of inhibiting the metabolism of cholesterol, comprising administering to a subject a dioxabicyclo[3.3.0]octane derivative represented by the following general formula (I):

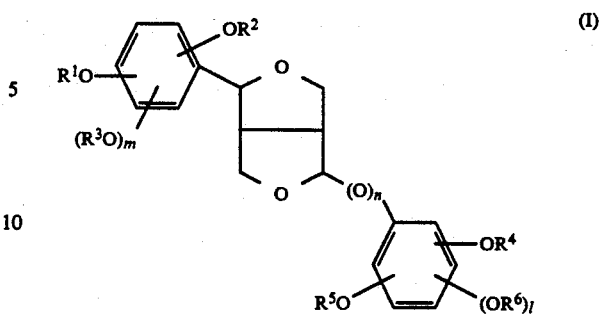

wherein $R^1$, $R^2$, $R^3$, $R^4$, $R^5$ and $R^6$ independently represent a hydrogen atom or an alkyl group having 1 to 3 carbon atoms, or $R^1$ and $R^2$ and/or $R^4$ and $R^5$ together form a methylene group or an ethylene group, and n, m and l are 0 or 1.

The present invention still further provides the use of the above-mentioned dioxabicyclo[3.3.0]octane derivative to produce a pharmaceutical preparation usable for an inhibition of the metabolism of cholesterol.

DESCRIPTION OF THE PREFERRED EMBODIMENTS

As the dioxabicyclo[3.3.0]octane derivative, in the present invention, sesamin, sesaminol, episesamin, episesaminol, sesamolin, 2-(3,4-methylenedioxyphenyl)-6-(3-methoxy-4-hydroxyphenyl)-3,7-dioxabicyclo-[3.3.0]octane, 2,6-bis-(3-methoxy-4-hydroxyphenyl)-3,7-dioxabicyclo[3.3.0]octane or 2-(3,4-methylenedioxyphenyl)-6-(3-methoxy-4-hydroxyphenoxy)-3,7-dioxabicyclo [3.3.0]octane can be used. These derivatives can be used alone or in the form of a mixture of two or more thereof.

The compound used in the present invention, and an extract composed mainly of the compound of the present invention, can be obtained according to the following procedures. First, an extract composed mainly of the compound of the present invention can be obtained from sesame oil according to a method comprising extracting sesame oil with an organic solvent substantially immiscible with sesame oil and capable of extracting and dissolving the compound of the present invention, and concentrating the extract. As the organic solvent, there can be mentioned, for example, acetone, methylethylketone, diethylketone, methanol and ethanol. For example, an extract composed mainly of the compound of the present invention can be obtained by mixing sesame oil homogeneously with an organic solvent as mentioned above, allowing the mixture to stand at a low temperature, carrying out a phase separation according to a customary process, and removing the solvent from the solvent fraction by evaporation.

More specifically, sesame oil is dissolved in 2 to 10 volumes, preferably 6 to 8 volumes of acetone, and the solution is allowed to stand at −80° C. overnight. As a result, the oil component is precipitated, and the organic solvent is removed from the obtained filtrate by distillation, whereby an extract composed mainly of the compound of the present invention is obtained. Alternatively, sesame oil is mixed with hot methanol or hot ethanol, the mixture is allowed to stand at room temperature, and the solvent is removed from the solvent fraction to obtain an extract composed mainly of the compound of the present invention. More specifically, sesame oil is mixed with hot methanol (higher than 50° C) or hot ethanol (higher than 50°) in a volume 2 to 10 times, preferably 5 to 7 times, as large as the volume of the sesame oil to effect a violent extraction. The phase separation is effected by a phase separation when standing at room temperature or a centrifugal separation according to customary procedures, and the solvent is removed from the solvent fraction by distillation to obtain an extract composed mainly of the compound of the present invention. Furthermore, the supercritical gas extraction can be utilized.

The compound of the present invention can be obtained from an extract as mentioned above by treating the extract by a customary method such as column chromatography, high performance liquid chromatography, recrystallization, distillation, or liquid-liquid countercurrent distribution chromatography. More specifically, by using a reversed phase column ($5C_{18}$) and methanol/water (60/40) as the eluent, the extract is subjected to high performance liquid chromatography, the solvent is removed by distillation, and the obtained crystal is recrystallized from ethanol to obtain the compound used in the present invention, such as sesamin, episesamin, sesaminol or episesaminol. The sesame oil used in the present invention can be either a purified product or a crude product. Furthermore, sesame seeds or sesame lees (defatted sesame seeds having a residual oil content of 8 to 10%) can be used. In this case, sesame seeds or sesame lees are pulverized if necessary, and then subjected to the extraction according to customary procedures using an any solvent, for example, a solvent as mentioned above with respect to the extraction from sesame oil. The extraction residue is separated, and the solvent is removed from the extract by evaporation or the like to obtain an extraction product.

The compound used in the present invention, for example, sesamin, sesaminol, episesamin, episesaminol, sesamolin, 2-(3,4-methylene-dioxyphenyl)-6-(3-methoxy4-hydroxyphenyl)-3,7-dioxabicyclo[3.3.0]octane, 2,6-bis-(3-methoxy-4-hydroxyphenyl)-3,7-dioxabicyclo [3.3.0]octane or 2-(3,4-methylenedioxyphenyl)-6-(3-methoxy-4-hydroxyphenoxy)-3,7-dioxabicyclo[3.3.-0]octane, can be obtained from a sesame seed extract, a sesame lee extract or a crude sesame oil extract according to the same procedures as described above. Moreover, the compound used in the present invention can be obtained from a by-product formed in the sesame oil-preparing process.

Note, sesamin obtained from Piper Longum L exhibits the same effects as those provided by sesame seeds, sesame bran and sesame oil.

The process for the purification of the compound used in the present invention and the process for obtaining the extract are not limited to those mentioned above, and the compound used in the present invention and the extract composed mainly of the compound of the present invention are not limited to those obtained from sesame oil, sesame lees and sesame seeds, but as is apparent to persons with ordinary skill in the art, all natural substances containing the compound used in the present invention can be used. For example, there can be mentioned *Acanthopanax ghacilistylus,* Asari Herba Cum Redice, *Ginkgo-bioloba* and *Piper longum* L.

The following processes can be adopted for the synthesis of the compound of the present invention.

For example, sesamin and episesamin can be synthesized according to the process of Beroza et al. [J. Am Chem. Soc., 78,1242 (1956)]. Pinoresiniol [in the general formula (I), $R^1$ and $R^4$ represent H, $R^2$ and $R^5$ represent $CH_3$, and n, m and l are zero] can be synthesized according to the process of Freundenberg et al. [Chem. Ber., 86, 1157 (1953)]. Furthermore, syringaresinol [in the general formula (I), $R^1$ and $R^4$ represent H, $R^2$, $R^3$, $R^4$, $R^5$ and $R^6$ represents $CH_3$, n is zero, and each of m and l is 1] can be synthesized according to the process of Freundenberg et al [Chem. Ber., 88, 16 (1955)].

The compound used in the present invention also can be used in the form of a glycoside. Furthermore, compounds used in the present invention can be used alone or in combination with other cholesterol metabolism inhibitor or a functional factor of a food.

The cholesterol metabolism inhibitor of the present invention can be orally administered, or non-orally administered, for example, by intramuscular injection, hypodermic injection or intravenous injection.

The dosage depends on the state of a person to whom the cholesterol metabolism inhibitor is administered, but in general, in the case of an administration, the dosage is 1 to 100 mg/day, and in the case of a non-oral administration, the dosage is 0.1 to 20 mg/day. For the preparation of an injection, a solubilizing agent for a drug, for example, a nonionic surface active agent, can be used. More specifically, the compound of the present invention is dissolved under heating in a nonionic surface active agent such as POE(60) hardened castor oil or POE sorbitan-monooleate in a volume 80 times as large as the volume of the compound of the present invention, and the solution is diluted with a physiological saline to form an injection solution. An isotonic agent, a stabilizer, an antiseptic agent, and an analgesic agent, can be incorporated according to need. If necessary, the compound of the present invention can be formed into an emulsion, a capsule, a powder, a granule or a tablet.

The present invention also provides a novel food comprising dioxabicycol[3.3.0]octane derivative, for inhibition of cholesterol metabolism. Since compounds for effective ingredients for the present invention are those found in foods or related compounds thereof, and therefore, they are advantageous in an aspect of safety.

The kind of foods to which the present compound is added is not limited. Moreover, an amount of dioxabicyclo[3.3.0]octane derivative is not critical, and preferably disxabicyclo[3.3.0]octane derivatives alone or in combination are added at a total amount of at least 0.0001%, and preferably at least 0.001% by weight. Moreover, where an extract containing dioxabicyclo [3.3.0]octane derivatives are used, they are used in an amount of at least 0.0004%, preferably 0.004% by weight.

EXAMPLES

Next, the present invention is further described in the following Examples.

EXAMPLE 1

First, 24 male Wister rats 4 weeks old and weighing 139 g were divided into 4 groups of 6 rats. One group was fed with an ordinary feed comprising 20% casein, 10% corn oil, 1% vitamin mixture (AIN-TM), 3.5% mineral mixture (AIN-TM), 0.2% choline bitartarate, 0.2% DL-methionine, 5% cellulose, 15% corn starch, and 45% sucrose; the second group was fed with the same ordinary feed except that the feed contained a 44.5% sucrose and an additional 0.5% cholesterol; the third group was fed with the same ordinary feed except that the feed contained 44.5% sucrose and an additional 0.5% sesamin; and the fourth group was fed with the same ordinary feed except that the feed contained 44.0% sucrose and an additional 0.5% cholesterol and 0.5% sesamin. Three weeks later, feces and urine were collected for 2 days, and the amounts of cholesterol in the feces and urine were determined.

The results is shown in Table 1. Moreover, an excretion of acidic steroids was measured, and the result is shown in Table 2.

TABLE 1

| Cholesterol in feces and urine | Ordinary feed | Ordinary feed + sesamin | Ordinary feed + cholesterol | Ordinary feed + cholesterol + sesamin |
|---|---|---|---|---|
| Amount of excretion (mg/day) Neutral steroids | | | | |
| Coprostanol | $4.15 \pm 0.60^a$ | $0.69 \pm 0.18^b$ | $13.3 \pm 1.3^c$ | $0.43 \pm 0.05^b$ |
| Cholesterol | $3.84 \pm 0.36^a$ | $8.44 \pm 0.38^b$ | $35.0 \pm 4.6^c$ | $71.0 \pm 4.8^d$ |
| Total | $7.99 \pm 0.96^a$ | $9.13 \pm 0.40^a$ | $48.3 \pm 5.6^b$ | $71.4 \pm 4.8^c$ |

The suffixes a, b, c, and d denote the presence of significant differences $p < 0.05$ between different letters on the same line.

TABLE 2

| Cholesterol in feces and urine | Ordinary feed | Ordinary feed + sesamin | Ordinary feed + cholesterol | Ordinary feed + cholesterol + sesamin |
|---|---|---|---|---|
| Acidic steroids | | | | |
| Lithocholic acid | $1.08 \pm 0.41^a$ | $4.97 \pm 0.70^b$ | $1.29 \pm 0.16^a$ | $3.92 \pm 0.39^b$ |
| Deoxycholic acid | $1.57 \pm 0.47$ | n.d. | $1.95 \pm 0.25$ | n.d. |
| Chenodeoxycholic acid | $0.04 \pm 0.02^a$ | $0.23 \pm 0.06^b$ | $0.07 \pm 0.03^{ab}$ | $0.14 \pm 0.06^{ab}$ |
| Hyodeoxycholic acid + Ursodeoxycholic acid | $3.78 \pm 1.71^a$ | n.d. | $0.88 \pm 0.41^{ab}$ | $0.10 \pm 0.06^b$ |
| Cholic acid | $0.21 \pm 0.09^a$ | $0.59 \pm 0.17^a$ | $0.18 \pm 0.13^a$ | $1.90 \pm 0.26^b$ |
| 12-ketomuricholic acid | $0.02 \pm 0.01^a$ | $0.20 \pm 0.04^a$ | $0.18 \pm 0.04^a$ | $1.10 \pm 0.20^b$ |
| α-Muricholic acid | $0.98 \pm 0.39^a$ | $0.25 \pm 0.13^a$ | $6.17 \pm 1.21^b$ | $0.61 \pm 0.21^a$ |
| β-Muricholic acid | $0.59 \pm 0.23^a$ | $0.58 \pm 0.17^a$ | $9.69 \pm 2.37^b$ | $7.81 \pm 1.31^b$ |
| Total | $8.30 \pm 2.22^{ab}$ | $6.86 \pm 1.02^a$ | $20.8 \pm 2.6^c$ | $15.9 \pm 1.9^{bc}$ |

The suffixes a, b, c, and d denote the presence of significant differences $p < 0.05$ between different letters on the same line.

The metabolism of cholesterol was inhibited by the administration of sesamin, and this effect was more strongly exhibited in the cholesterol-administered group.

It is known that coprostanol is one of the sterols still present in human feces as a sterol, and is produced from cholesterol via cholestenon (4-cholesten3-on) during the passage of cholesterol in the digestion truck. In this Example, coprostanol, which is relatively stable among the cholesterol metabolites, was used as an indication of cholesterol metabolism. As seen from Table 1, the concomitant intake of cholesterol and sesamin remarkably lowers the excretion of coprostanol in comparison with an intake of cholesterol alone, and increases the excretion of cholesterol. This suggests that sesamin inhibits the metabolism of cholesterol.

EXAMPLE 2

First, 36 male Wister rats 4 weeks old and weighing 139 g were divided into 6 groups of 6 rats. One group was fed with a cholesterol feed comprising 20% casein, 10% corn oil, 1% vitamin mixture (AIN-TM), 3.5% mineral mixture (AIN-TM), 0.2% choline bitartrate, 0.3% DL-methionine, 5% cellulose, 15% corn starch, 0.5% cholesterol and 44.5% sucrose. The other five groups were fed with the same feed as the above-mentioned cholesterol feed except that the feed contained 44.0% sucrose, and contained sesaminol (Compound A) prepared from a refined sesame oil according to a procedure described in Japanese Patent Application No. 63-53642; sesamolin (Compound B) prepared from crude sesame oil; or 2-(3,4-methylenedioxyphenyl)-6-(3-methoxy-4-hydroxyphenyl)-3,7-dioxabicyclo[3.3.0]octane (Compound C); 2,6-bis-(3-methoxy-4-hydroxyphenyl)-3,7-dioxabicyclo [3.3.0]octane (Compound D) or 2-(3,4-methylenedioxyphenyl)-6-(3-methoxy-4-hydroxyphenoxy)-3,7-dioxabicyclo [3.3.0]octane (Compound E) prepared from sesame seeds, in an amount of 0.5%, respectively. Three weeks later, feces and urine were collected for 2 days, and the amount of sterol in the feces and urine was analyzed. The amount of cholesterol in the feces and urine from the cholesterol feed was $35.0 \pm 4.6$ mg/day; and the cholesterol was increased to $68.4 \pm 4.4$, $66.3 \pm 4.9$, $67.1 \pm 5.1$, $62.5 \pm 4.3$ and $64.7 \pm 3.9$ for feeds containing Compounds A, B, C, D or E, respectively. The amount of coprostanol in the feces and urine was $13.3 \pm 3$ for the cholesterol feed; and the amount of coprostanol was reduced to $0.63 \pm 0.07$, $0.93 \pm 0.11$, $0.84 \pm 0.05$, $0.79 \pm 0.08$ and $1.12 \pm 0.09$, for feeds containing the Compounds A, B, C, D or E, respectively.

EXAMPLE 3

To 20 ml of water was added 2 g of β-cyclodextrin, and 0.2 g of sesamin dissolved in a small amount of acetone was added to the mixture under agitation by a stirrer. The mixture was stirred at room temperature for 4 hours and freeze-dried to obtain 2.2 g of a cyclodextrin inclusion compound containing 10% of sesamin. A sesamin-containing juice was prepared by adding 1 g of the obtained powder to 100 ml of a juice.

EXAMPLE 4

The procedures of Example 3 were repeated by using the compound of the present invention and the extract composed mainly of the compound of the present invention. Juices containing the compound of the present invention and the extract, respectively, were obtained.

EXAMPLE 5

In 82 g of a starting oil and fat material comprising 30% of edible hardened soybean oil, 10% of edible hardened cotton seed oil, 40% of soybean salad oil, 10% of palm oil and 10% of corn oil, 1 g of sesamin was incorporated and dissolved. Then, 15 g of water, 1.2 g of table salt, 0.3 g of monoglyceride, 0.1 g of lecithin, a trace of carotene, 0.00001 g of a flavor and 1.4 g of a milk solid were added to the solution, and the mixture was emulsified, rapidly cooled, and kneaded to obtain a sesamin-containing margarin.

We claim:

1. A method of inhibiting the catabolism of cholesterol, comprising administering to a patient in need of such treatment, a dioxabicyclo[3.3.0]octane derivative represented by the following general formula (I):

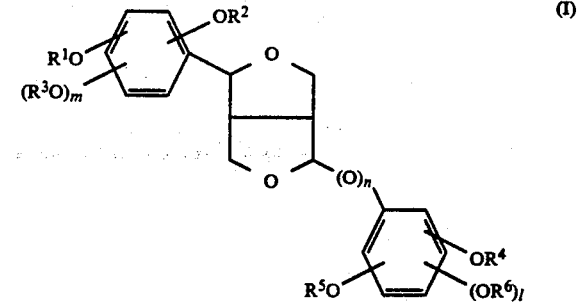

wherein $R^1$, $R^2$, $R^3$, $R^4$, $R^5$ and $R^6$ independently represent a hydrogen atom or an alkyl group having 1 to 3 carbon atoms, or $R^1$ and $R^2$ and/or $R^4$ and $R^5$ together form a methylene group of an ethylene group, and n, m and $\gamma$ are 0 or 1, in an effective amount to inhibit the catabolism of cholesterol.

2. A method according to claim 1, wherein the dioxabicycooctane derivative is sesamin, sesaminol, epixesamin, episesaminol, sesamolin, 2-(3,4-methylenedioxphenyl)-6-(3-methoxy-4-hydroxyphgenyl)-3,7-dioxabicyclooctane, 2,6-bis-(3-methoxy-4-hydroxyphenyl)-3,7-dioxabicycooctane or 2-(3,4-methylenedioxyphenyl)-6-(3-methoxy-4-hydroxyphenoxy)-3,7-dioxabicyclooctane.

3. The method according to claim 1, wherein the amount of dioxabicyclooctane derivative is administered orally in the amount of 1 to 100 mg/day.

4. The method according to claim 1, wherein the amount of dioxabicycooctane derivative is administered non-orally in the amount of 0.1 to 20 mg/day.

* * * * *

UNITED STATES PATENT AND TRADEMARK OFFICE
CERTIFICATE OF CORRECTION

PATENT NO. : 5,270,335

DATED : December 14, 1993

INVENTOR(S) : Kengo AKIMOTO et al

It is certified that error appears in the above-indentified patent and that said Letters Patent is hereby corrected as shown below:

At Column 1, lines 9-10, please amend "dioxabicyclo [33.0] octane" to --dioxabicyclo [3.3.0] octane--.

At Column 8, lines 21-22, please amend "dioxabicycooctane" to --dioxabicyclo [3.3.0] octane--.

At Column 8, lines 22-23, please amend "epixesamin" to --episesamin--.

At Column 8, line 24, please amend "hydroxyphgenyl" to --hydroxyphenyl--.

At Column 8, lines 24-25, please amend "dioxabicyclooctane" to --dioxabicyclo [3.3.0] octane--.

At Column 8, line 26, please amend "dioxabicycooctane" to --dioxabicyclo [3.3.0] octane--.

At Column 8, lines 27-28, please amend "dioxabicyclooctane" to --dioxabicyclo [3.3.0] octane--.

At Column 8, line 30, please amend "dioxabicyclooctane" to --dioxabicyclo [3.3.0] octane--.

UNITED STATES PATENT AND TRADEMARK OFFICE
CERTIFICATE OF CORRECTION

PATENT NO. : 5,270,335

DATED : December 14, 1993

INVENTOR(S) : Kengo AKIMOTO et al

It is certified that error appears in the above-indentified patent and that said Letters Patent is hereby corrected as shown below:

At Column 8, line 33, please amend "dioxabicyclooctane" to --dioxabicyclo [3.3.0] octane--.

Signed and Sealed this

Twelfth Day of July, 1994

*Attest:*

BRUCE LEHMAN

*Attesting Officer*     Commissioner of Patents and Trademarks